United States Patent [19]

Kamata et al.

[11] Patent Number: 4,605,738
[45] Date of Patent: Aug. 12, 1986

[54] PRODUCTION OF 1-PHTHALIDYL-5-FLUOROURACIL DERIVATIVES

[75] Inventors: Susumu Kamata, Hyogo; Nobuhiro Haga, Osaka; Wataru Nagata, Hyogo; Takeaki Matsui, Osaka, all of Japan

[73] Assignee: Shionogi & Co., Ltd., Osaka, Japan

[21] Appl. No.: 550,219

[22] Filed: Nov. 9, 1983

[30] Foreign Application Priority Data

Nov. 18, 1982 [JP] Japan ................................ 57-203482

[51] Int. Cl.[4] ................... C07D 239/10; C07D 307/83
[52] U.S. Cl. .................................... 544/310; 544/153; 544/313; 549/303; 549/307; 549/310
[58] Field of Search ....................... 544/313, 310, 153; 549/153, 303

[56] References Cited

U.S. PATENT DOCUMENTS 2,997,481  8/1961  Wheeler .............................. 549/303
3,284,468  11/1966  Keller ................................. 544/153

FOREIGN PATENT DOCUMENTS 016881  1/1982  Japan ................................. 544/310
57-32271  2/1982  Japan .
032270  2/1982  Japan ................................. 544/310
1425295  2/1976  United Kingdom ................ 544/153

OTHER PUBLICATIONS

Burger, "Medicinal Chemistry", 2nd Edition, pp. 1130-1134.
Chemical Abstracts, 97:92302d & 92305g, (1982) (Shionogi).

*Primary Examiner*—Robert Gerstl
*Assistant Examiner*—Stephen M. Kapner
*Attorney, Agent, or Firm*—Wenderoth, Lind & Ponack

[57] ABSTRACT

Highly selective and high yield process for producing antitumor agent 1-phthalidyl-5-fluorouracil derivatives of formula (I) which comprises reacting a phthalidyl compound (II) with an amine (III) to yield the quaternary ammonium salts (IV), and reacting the latter with 5-fluorouracil.

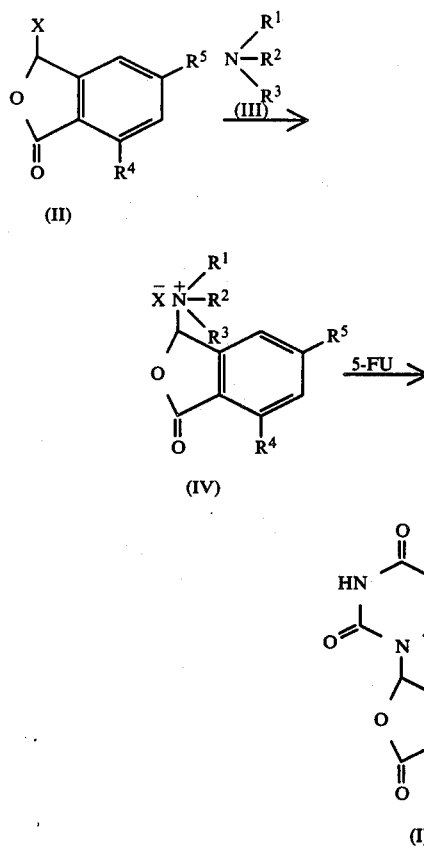

[wherein X is leaving group;

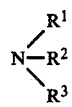

is triethylamine, N-methylmorpholine, N-ethylmorpholine, and the like; $R^4$ and $R^5$ each is hydrogen, trialkylsilyloxy, alkoxy, nitro, cyano, carboxy, or alkoxycarbonyl].

6 Claims, No Drawings

PRODUCTION OF 1-PHTHALIDYL-5-FLUOROURACIL DERIVATIVES

BACKGROUND OF THE INVENTION

1. Field of the Invention

The present invention relates to a new process for producing 1-phthalidyl-5-fluorouracil derivatives which comprises reacting phthalidylammonium derivatives with 5-fluorouracil (hereinafter abbreviated as to 5-FU). The compounds of the present invention are known to have potent antitumor activity and can be utilized as antitumor agents for humans and animals, and they are particularly useful in treatment of various malignant tumors.

2. Description of the Prior Art

The 1-phthalidyl-5-fluorouracil derivatives of the present invention are known to have potent antitumor activity and can be utilized as antitumor agents for humans and animals, and they are particularly useful in treatment of or prophylaxis of metastases of malignant tumors such as uterine cancer, esophagus carcinoma, cutaneous cancer, gastric cancer, lung cancer, liver cancer, colic and rectum cancer, pancreas cancer, mammary cancer, bladder cancer, trophoblastic neoplasia, cerebral tumor, lymphosarcoma, leukemia, and the like [Japanese Unexamined Patent Publication Nos. 57-16881 and 57-67578].

In the prior art, the 5-fluorouracil derivatives have been prepared in the following ways.

(1) Reaction of 5-FU with 3-halophthalide in the presence of an organic or inorganic base [Japanese Unexamined Patent Publication No. 57-16881].

(2) Reaction of 5-FU with 3-trifluoroacetylphthalide [Japanese Patent Application No. 57-181047].

BRIEF SUMMARY OF THE INVENTION

The present invention relates to a process for producing a 1-phthalidyl-5-fluorouracil derivative. More particularly, it relates to a process for producing a 1-phthalidyl-5-fluorouracil derivative represented by the general formula (I):

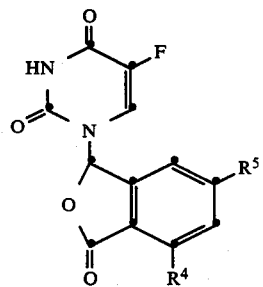

[wherein $R^4$ and $R^5$ each represents hydrogen, trialkylsilyloxy, alkoxy, nitro, cyano, carboxy, or alkoxycarbonyl] which comprises reacting a phthalidyl compound represented by the general formula (II):

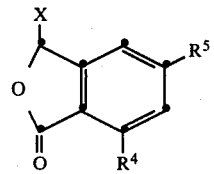

[wherein X represents halogen, trihalogenoacetyloxy, alkylsulfonyloxy, or arylsulfonyloxy; $R^4$ and $R^5$ each has the same significance as defined above]
with a tertiary amine represented by the general formula (III):

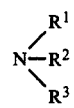

[wherein $R^1$, $R^2$, and $R^3$ each represents alkyl, or $R^1$ represents alkyl, and $R^2$ and $R^3$ taken together with the adjacent nitrogen atom form a saturated 5- or 6-membered ring which may contain an oxygen, or

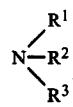

represents quinuclidine]
to yield a phthalidylammonium compound represented by the general formula (IV):

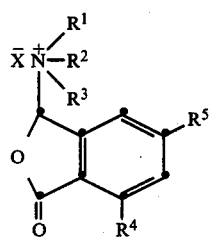

[wherein X, $R^1$, $R^2$, $R^3$, $R^4$, and $R^5$ each has the same significance as defined above] and reacting the latter with 5-FU. The present invention also relates to a process for producing a 1-phthalidyl-5-fluorouracil derivative represented by the general formula (I):

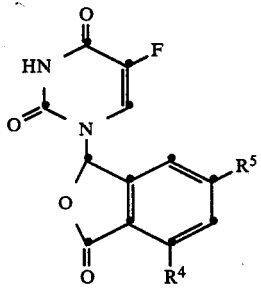

[wherein $R^4$ and $R^5$ each has the same significance as defined above]
which comprises adding a tertiary amine represented by the general formula (III):

[wherein $R^1$, $R^2$, and $R^3$ each has the same significance as defined above]
to a phthalidyl compound represented by the general formula (II):

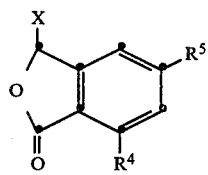

[wherein X, $R^4$, and $R^5$ each has the same significance as defined above]
and then allowing to react with 5-FU.

The present inventors have investigated to develop a new improved process for producing 1-phthalidyl-5-fluorouracil derivatives; the present invention is based on the result of the investigation.

DETAILED DESCRIPTION OF THE PREFERRED EMBODIMENTS OF THE INVENTION

The definition relating to the general formulas (I)–(IV) shown in the brief summary of the invention is: the halogen includes fluorine, chlorine, bromine and iodine; the trihalogenoacetyloxy includes trifluoroacetyloxy, trichloroacetyloxy, tribromoacetyloxy, etc.;
the alkylsulfonyloxy is a $C_1$–$C_5$ alkylsulfonyloxy including methylsulfonyloxy, ethylsulfonyloxy, propylsulfonyloxy, isopropylsulfonyloxy, butylsulfonyloxy, isobutylsulfonyloxy, t-butylsulfonyloxy, pentylsulfonyloxy, isopentylsulfonyloxy, neopentylsulfonyloxy, t-pentylsulfonyloxy, etc.;
the arylsulfonyloxy includes benzenesulfonyloxy, p-toluenesulfonyloxy, p-bromobenzenesulfonyloxy, p-chlorobenzenesulfonyloxy, p-methoxybenzenesulfonyloxy, p-nitrobenzenesulfonyloxy, etc.;
the alkyl is a $C_1$–$C_5$ alkyl including methyl, ethyl, propyl, isopropyl, butyl, isobutyl, pentyl and isopentyl;
the saturated 5- or 6- membered ring which is formed together with the adjacent nitrogen atom and which may contain an oxygen, means piperidino, pyrrolidino, morpholino, and the like; the trialkylsilyloxy is a silyloxy substituted by three $C_1$–$C_4$ alkyls which may be the same or different each other, including trimethylsilyloxy, triethylsilyloxy, tripropylsilyloxy, dimethylethylsilyloxy, dimethylpropylsilyloxy, diethylmethylsilyloxy, methylethylpropylsilyloxy, dimethylbutylsilyloxy, dimethyl-t-butylsilyloxy, etc.;
the alkoxy is a $C_1$–$C_5$ alkoxy including methoxy, ethoxy, propoxy, isopropoxy, butoxy, isobutoxy, t-butoxy, pentyloxy, isopentyloxy, neopentyloxy, t-pentyloxy, etc.; the alkoxycarbonyl means those having alkoxy groups as mentioned above.

According to the present invention the objective compounds (I) can easily be produced from the starting compounds (II) through the intermediates (IV).

The intermediates (IV) can be produced by the reaction of the starting compounds (II) with tertiary amines (III) in the first step.

As the tertiary amines (III) used in the reaction, trimethylamine, triethylamine, tri-n-propylamine, tri-n-butylamine, N-methylpiperidine, N-ethylpiperidine, N-methylpyrrolidine, N-ethylpyrrolidine, N-methylmorpholine, N-ethylmorpholine, quinuclidine, and the like may be exemplified. The reaction is conducted in an appropriate solvent under ice-cooling or heating, and terminates within a period of several hours to several days.

As the solvent, an aprotic solvent such as dichloromethane, benzene, acetonitrile, tetrahydrofuran, dimethylformamide, dimethylacetamide, dimethylsulfoxide, and the like may be employed suitably, and in a certain case the reaction is promoted by addition of a catalytic amount of an appropriate reagent like sodium halide, potassium halide, or tetraalkylammonium halide. The intermediate of the general formula (IV) in the present invention in which X is halogen can be converted into the compounds in which X is trihalogenoacetyloxy, alkylsulfonyloxy, or arylsulfonyloxy, on reaction with the corresponding silver salts.

The intermediates (IV) provided in the first step are exemplified below:
N,N,N-triethyl-3-oxo-1,3-dihydro-1-isobenzofuranylammonium bromide,
N,N,N-triethyl-3-oxo-1,3-dihydro-1-isobenzofuranylammonium chloride,
4-Methyl-4-(3-oxo-1,3-dihydro-1-isobenzofuranyl)-morpholinium bromide,
4-Methyl-4-(3-oxo-1,3-dihydro-1-isobenzofuranyl)-morpholinium chloride,
4-Ethyl-4-(3-oxo-1,3-dihydro-1-isobenzofuranyl)-morpholinium bromide.

In the next step, the objective compounds (I) can be produced by the reaction of the intermediates (IV) with 5-FU. The reaction is conducted in an appropriate solvent in the presence of a base at room temperature or under heating, and terminates within a period of several hours to several days.

As the solvent an aprotic solvent, acetonitrile, tetrahydrofuran, dimethylformamide, dimethylacetamide, dimethylsulfoxide, and the like may be employed suitably, preferably, dimethylformamide, or dimethylsulfoxide is used. As the base, an organic base, e.g. triethylamine, tri-n-butylamine, diisopropylethylamine, N-methylpiperidine, N-ethylpiperidine, N-methylpyrrolidine, N-ethylpyrrolidine, N-methylmorpholine, N-ethylmorpholine, quinuclidine, pyridine, dimethylaminopyridine, picoline, cholidine, dimethylaniline, and the like, and an inorganic base, e.g. potassium carbonate, sodium carbonate, and the like may be exemplified.

In the above reaction, the intermediates (IV) which is previously produced by the reaction of the starting compounds (II) with a tertiary amine (III) without isolation in this step, can be allowed to react directly with 5-FU in the presence of the same tertiary amine or an appropriate other base. The whole reactions can be conducted in a single reaction vessel by a simple operation.

The starting compounds (II) are commercially available or otherwise can easily be produced by the known method described in literatures [for example, Japanese Unexamined Patent Publication No. 57-16881].

The process of the present invention is advantageous in high selectivity to and high yield of the N(1)-substituted-5-fluorouracil accompanied with a negligible amount of the by-product N(1),N(3)-disubstituted-5-fluorouracil in comparison with the known method as described in Japanese Unexamined Patent Publication No. 57-16881 in which 3-halogenophthalides are used as starting compounds and are allowed to react directly with 5-FU, not through the intermediates (IV).

The compounds provided by the process of this invention are exemplified below:
1-(3-Oxo-1,3-dihydro-1-isobenzofuranyl)-5-fluorouracil,
1-(3-Oxo-6-trimethylsilyloxy-1,3-dihydro-1-isobenzofuranyl)-5-fluorouracil,
1-(3-Oxo-6-triethylsilyloxy-1,3-dihydro-1-isobenzofuranyl)-5-fluorouracil,
1-(3-Oxo-6-t-butyldimethylsilyloxy-1,3-dihydro-1-isobenzofuranyl)-5-fluorouracil,
1-(3-Oxo-6-t-butyldiethylsilyloxy-1,3-dihydro-1-isobenzofuranyl)-5-fluorouracil,
1-(3-Oxo-6-methoxy-1,3-dihydro-1-isobenzofuranyl)-5-fluorouracil,
1-(3-Oxo-6-ethoxy-1,3-dihydro-1-isobenzofuranyl)-5-fluorouracil,
1-(3-Oxo-6-nitro-1,3-dihydro-1-isobenzofuranyl)-5-fluorouracil,
1-(3-Oxo-6-cyano-1,3-dihydro-1-isobenzofuranyl)-5-fluorouracil,
1-(3-Oxo-6-carboxy-1,3-dihydro-1-isobenzofuranyl)-5-fluorouracil,
1-(3-Oxo-6-methoxycarbonyl-1,3-dihydro-1-isobenzofuranyl)-5-fluorouracil,
1-(3-Oxo-6-ethoxycarbonyl-1,3-dihydro-1-isobenzofuranyl)-5-fluorouracil,
1-(3-Oxo-4-trimethylsilyloxy-1,3-dihydro-1-isobenzofuranyl)-5-fluorouracil,
1-(3-Oxo-4-t-butyldimethylsilyloxy-1,3-dihydro-1-isobenzofuranyl)-5-fluorouracil,
1-(3-Oxo-4-methoxy-1,3-dihydro-1-isobenzofuranyl)-5-fluorouracil,
1-(3-Oxo-4-ethoxy-1,3-dihydro-1-isobenzofuranyl)-5-fluorouracil,
1-(3-Oxo-4-nitro-1,3-dihydro-1-isobenzofuranyl)-5-fluorouracil,
1-(3-Oxo-4-cyano-1,3-dihydro-1-isobenzofuranyl)-5-fluorouracil,
1-(3-Oxo-4-carbonyl-1,3-dihydro-1-isobenzofuranyl)-5-fluorouracil,
1-(3-Oxo-4-methoxycarbonyl-1,3-dihydro-1-isobenzofuranyl)-5-fluorouracil,
1-(3-Oxo-4-ethoxycarbonyl-1,3-dihydro-1-isobenzofuranyl)-5-fluorouracil.

The present invention will be explained more in detail by the following Examples.

EXAMPLE 1

(1) Preparation of N,N,N-triethyl-3-oxo-1,3-dihydro-1-isobenzofuranylammonium bromide

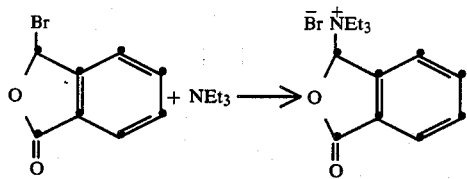

A mixture of 8.52 g (40 mmol) of 3-bromo-1,3-dihydro-1-isobenzofuranone 1 and 27.87 ml (200 mmol) of triethylamine in 85 ml of tetrahydrofuran is allowed to react at room temperature for 96 hours, and the precipitating crystals are filtered and washed with dichloromethane to give 11.04 g of the titled compound 2.
(Yield: 88%)
m.p. 173°–174° C.
NMR: $\delta d_6$DMSO 1.25 (t, J=8.0 Hz, 9H), 3.58 (q, J=8.0 Hz, 6H), 7.16 (s, 1H), 7.80–8.23 (m, 4H).
Elemental analysis (%) Calcd: C, 53.51; H, 6.42; N, 4.46 (for $C_{14}H_{20}NO_2Br$). Found: C, 53.07; H, 6.42; N, 4.52.

(2) Preparation of 1-(3-oxo-1,3-dihydro-1-isobenzofuranyl)-5-fluorouracil

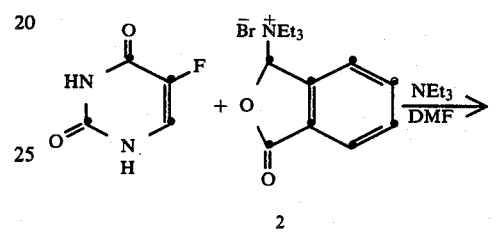

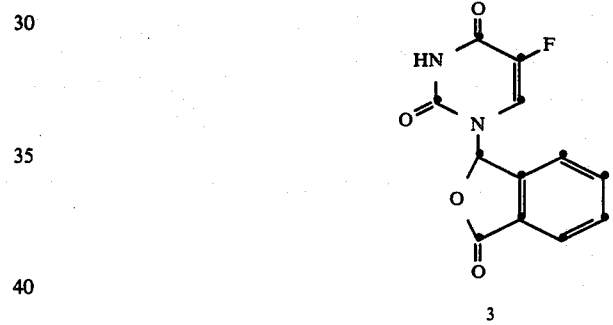

A solution of 3.14 g (10 mmol) of the compound 2 provided in the above step (1) and 1.3 g (10 mmol) of 5-FU dissolved in 26 ml of anhydrous dimethylformamide to which is added 0.14 ml (1 mmol) of triethylamine, is allowed to react at room temperature for 15 hours, and the reaction mixture is poured into 260 ml of ice-water containing 5 ml of 2N hydrochloric acid and stirred for 30 minutes. The precipitating crystals are collected by filtration to give 2.44 g of the titled compound 3 (Yield: 93%). This compound is recrystallized from dimethylsulfoxide-water to give white crystals m.p. higher than 290° C.
Elemental analysis (%) Calcd: C, 54.97; H, 2.69; N, 10.69; F, 7.24 (for $C_{12}H_7O_4N_2F$). Found: C, 54.95; H, 2.77; N, 10.38; F, 7.64.
IR: $\nu_{max}^{KBr}$ 1798, 1715, 1686, 1670 cm$^{-1}$.
UV: $\lambda_{max}^{EtOH}$ nm($\epsilon$) 227(17,400), 264(10,000).
NMR: $\delta d_6$DMSO 4.36 (broad, 1H), 7.5–8.2 (m, 4H), 7.56 (s, 1H), 7.67 (d, J=7 Hz, 1H).

EXAMPLE 2

(1) Preparation of N,N,N-triethyl-3-oxo-1,3-dihydro-1-isobenzofuranylammonium chloride

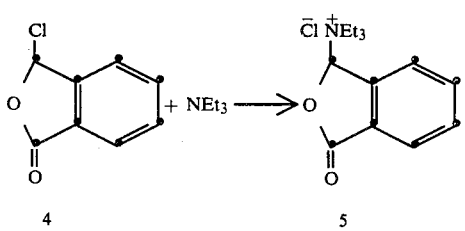

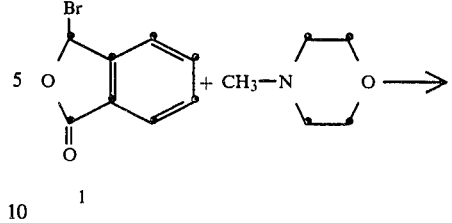

A mixture of 5.05 g (30 mmol) of 3-chloro-1,3-dihydro-1-isobenzofuranone 4, 12.5 ml (90 mmol) of triethylamine and 225 mg (1.5 mmol) of sodium iodide in 20 ml of acetonitrile is allowed to react with stirring under reflux for 7 hours. The solvent and excess amount of triethylamine are distilled off under reduced pressure, and the resulting residue is mixed with dichloromethane; the precipitating crystals are collected by filtration to give the titled compound 5 as crude crystals.

NMR: δd$_6$DMSO 1.24 (t, J=8.5 Hz, 9H), 3.59 (q, J=8.5 Hz, 6H), 7.23 (s, 1H), 7.80–8.27 (m, 4H).

(2) Preparation of 1-(3-oxo-1,3-dihydro-1-isobenzofuranyl)-5-fluorouracil

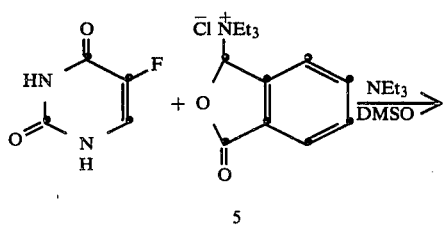

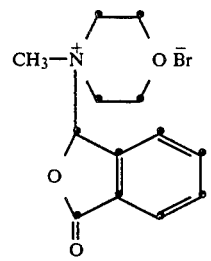

A solution of 927 mg (7.13 mmol) of 5-FU and 1 equimolar amount of the compound 5 provided in the above step (1) in 6 ml of anhydrous dimethylsulfoxide to which is added 0.5 ml (3.6 mmol) of triethylamine is allowed to react at room temperature for 15 hours, and the reaction mixture is poured into 100 ml of ice-water containing 5 ml of 2N hydrochloric acid, and stirred for 30 minutes. The precipitating crystals are collected by filtration to give 1.76 g of the titled compound 3. (Yield: 94%).

EXAMPLE 3

(1) Preparation of 4-methyl-4-(3-oxo-1,3-dihydro-1-isobenzofuranyl)morpholinium bromide A mixture of 5.34 g (25 mmol) of 3-bromo-1,3-dihydro-1-isobenzofuranone 1 and 2.75 ml (25 mmol) of N-methylmorpholine in 20 ml of benzene is allowed to react at room temperature for 70 hours, and the precipitating crystals are filtered and washed with benzene to give 6.52 g of the titled compound 6 (Yield: 83%).

m.p. 198°–200° C.

Elemental analysis (%) Calcd: C, 49.69; H, 5.13; N, 4.46; Br, 25.44 (for C$_{13}$H$_{16}$NO$_3$Br). Found: C, 49.14; H, 5.20; N, 4.64; Br, 25.17.

NMR: δd$_6$DMSO 3.03 (s, 3H), 3.4–4.2 (m, 8H), 7.33 (s, 1H), 7.8–8.3 (m, 4H).

(2) Preparation of 1-(3-oxo-1,3-dihydro-1-isobenzofuranyl)-5-fluorouracil

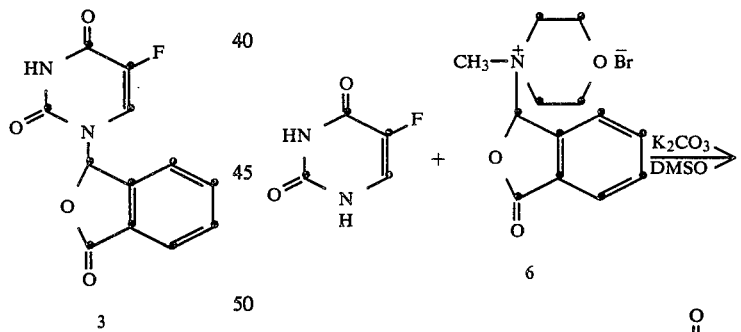

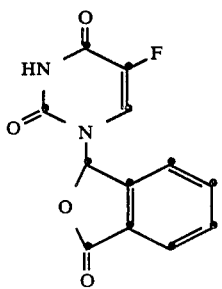

8.40 g (26.7 mmol) of the compound 6 provided in the above step (1), 3.48 g (26.7 mmol) of 5-FU, and 3.69 g (26.7 mmol) of anhydrous potassium carbonate are added to 35 ml of dimethylsulfoxide, and the mixture is allowed to react with stirring well at room temperature for 15 hours. The reaction mixture is poured into 350 ml of ice-water containing 27 ml of 2N hydrochloric acid, and stirred for about 15 minutes; the precipitating crystals are collected by filtration, washed with water (30 ml×3), methanol (30 ml×1), and ether (30 ml×1), and dried to give 6.56 g of the titled compound 3 (Yield: 94%).

EXAMPLE 4

(1) Preparation of 4-methyl-4-(3-oxo-1,3-dihydro-1-isobenzofuranyl)morpholinium chloride

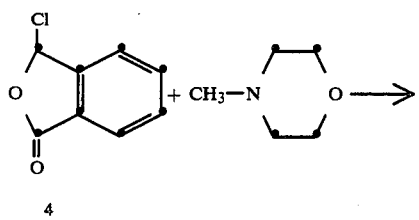

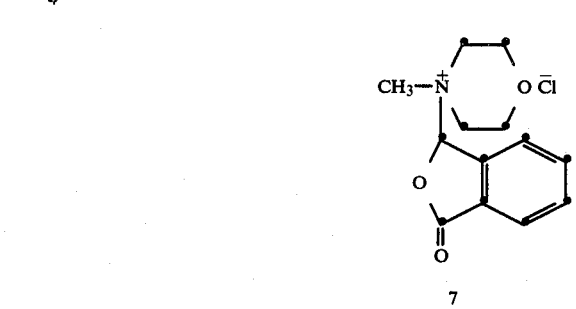

In the same manner as in Example 3-(1) the titled compound 7 is prepared.

NMR: δ d6DMSO 3.03 (s, 3H), 3.7-4.2 (m, 8H), 7.43 (s, 1H), 7.9-8.25 (m, 4H).

(2) Preparation of 1-(3-oxo-1,3-dihydro-1-isobenzofuranyl)-5-fluorouracil

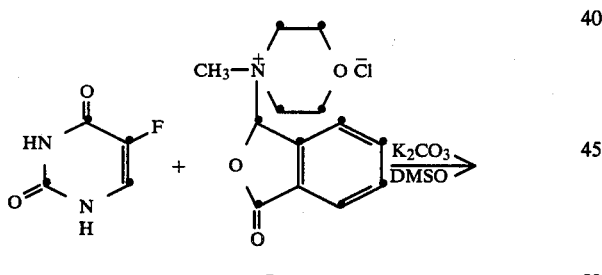

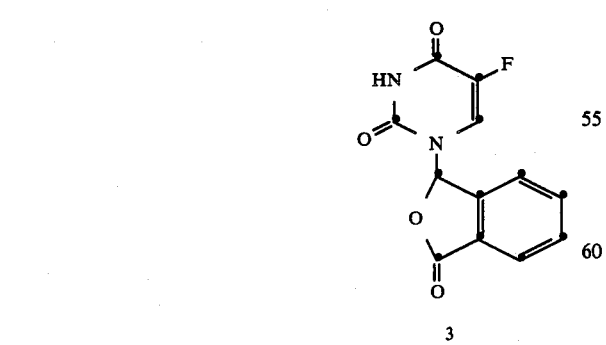

In the same manner as in Example 3-(2), a mixture of the compound 7 provided in the above step (1) and 5-FU in dimethylsulfoxide is allowed to react in the presence of 1 equimolar amount of anhydrous potassium carbonate at room temperature to give the titled compound 3 in good yield.

EXAMPLE 5

(1) Preparation of N,N,N-triethyl-3-oxo-1,3-dihydro-1-isobenzofuranylammonium trifluoroacetate

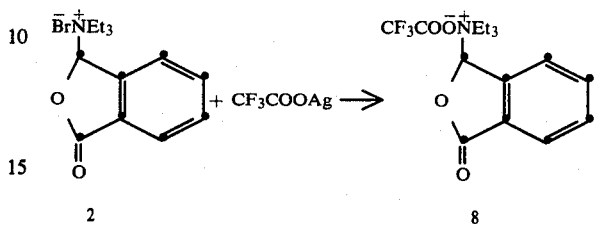

A mixture of 4.0 g (12.7 mmol) of N,N,N-triethyl-3-oxo-1,3-dihydro-1-isobenzofuranylammonium bromide 2 and 2.81 g (12.7 mmol) of silver trifluoroacetate in acetonitrile is allowed to react at room temperature for 63 hours, and the residue after removal of the solvent under reduced pressure is mixed with dichloromethane. The mixture is filtered in order to remove silver bromide, and the resulting filtrate is concentrated under reduced pressure to give the titled compound 8.

NMR: δ d6DMSO 1.23 (t, J=8.0 Hz, 9H), 3.56 (q, J=8.0 Hz, 6H), 7.07 (s, 1H), 7.80–8.27 (m, 4H).

(2) Preparation of 1-(3-oxo-1,3-dihydro-1-isobenzofuranyl)-5-fluorouracil

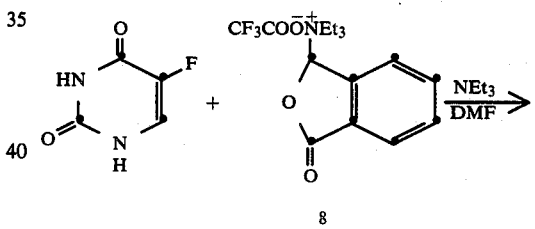

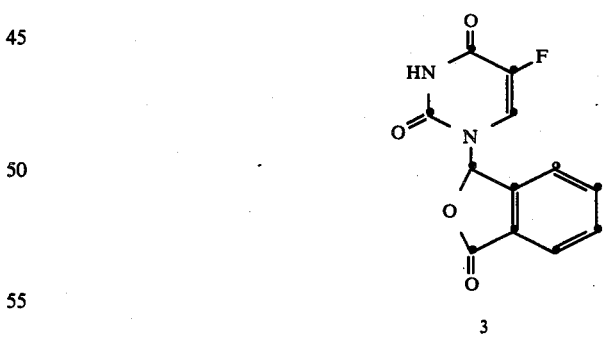

The compound 8 as crude product provided in the above step (1) and 1.66 g (12.7 mmol) of 5-FU are dissolved in 32 ml of anhydrous dimethylformamide, and the solution to which is added 0.18 ml (1.27 mmol) of triethylamine is allowed to react at room temperature for 15 hours; the reaction mixture is poured into 320 ml of ice-water containing 7 ml of 2N hydrochloric acid and stirred for 30 minutes. The precipitating crystals are filtered to give 3.16 g of the titled compound 3 (Yield: 95%).

EXAMPLE 6

(1) Preparation of N,N,N-triethyl-3-oxo-1,3-dihydro-1-isobenzofuranylammonium methanesulfonate

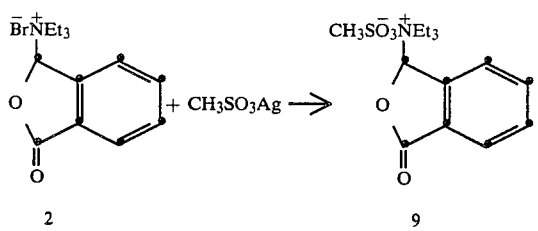

A mixture of 2.13 g (6.78 mmol) of N,N,N-triethyl-3-oxo-1,3-dihydro-1-isobenzofuranylammonium bromide 2 and 1.38 g (6.78 mmol) of silver methanesulfonate in acetonitrile is allowed to react for 15 hours, and the residue after removal of the solvent under reduced pressure is mixed with dichloromethane and filtered in order to remove silver bromide. The resulting filtrate is concentrated under reduced pressure to give the titled compound 9.

NMR: δ d$_6$DMSO 1.23 (t, J=8.0 Hz, 9H), 2.30 (s, 3H), 3.55 (q, J=8.0 Hz, 6H), 7.03 (s, 1H), 7.80–8.25 (m, 4H).

(2) Preparation of 1-(3-oxo-1,3-dihydro-1-isobenzofuranyl)-5-fluorouracil

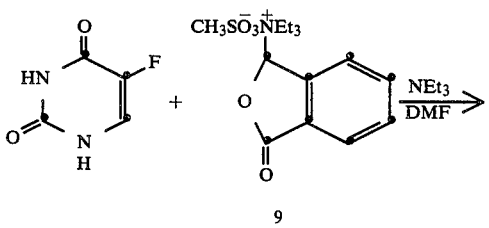

The compound 9 as crude product provided in the above step (1) and 0.881 g (6.78 mmol) of 5-FU are dissolved in 16 ml of anhydrous dimethylformamide, and the solution to which is added 94 μl (0.678 mmol) of triethylamine is allowed to react at room temperature for 15 hours; the reaction mixture is poured into 160 ml of ice-water containing 4 ml of 2N hydrochloric acid and stirred for 30 minutes. The precipitating crystals are filtered to give 1.68 g of the titled compound 3 (Yield: 95%).

EXAMPLE 7

(1) Preparation of N,N,N-triethyl-3-oxo-1,3-dihydro-1-isobenzofuranylammonium p-toluenesulfonate

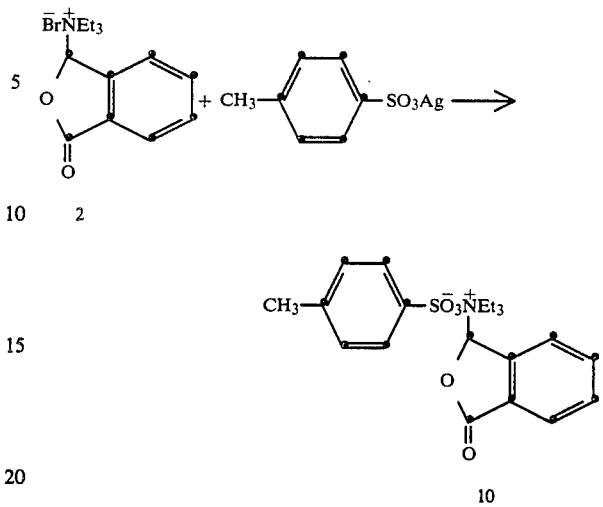

A mixture of 1.87 g (5.95 mmol) of N,N,N-triethyl-3-oxo-1,3-dihydro-1-isobenzofuranylammonium bromide 2 and 1.62 g (5.95 mmol) of silver p-toluenesulfonate in acetonitrile is allowed to react for 15 hours, and the residue after removal of the solvent under reduced pressure is mixed with dichloromethane and is filtered in order to remove silver bromide. The resulting filtrate is concentrated under reduced pressure to give the titled compound 10.

NMR: δ d$_6$DMSO 1.22 (t, J=8.0 Hz, 9H), 2.27 (s, 3H), 3.53 (q, J=8.0 Hz, 6H), 7.00 (s, 1H), 7.10 (d, J=8.0 Hz, 2H), 7.50 (d, J=8.0 Hz, 2H), 7.80–8.23 (m, 4H).

(2) Preparation of 1-(3-oxo-1,3-dihydro-isobenzofuranyl)-5-fluorouracil

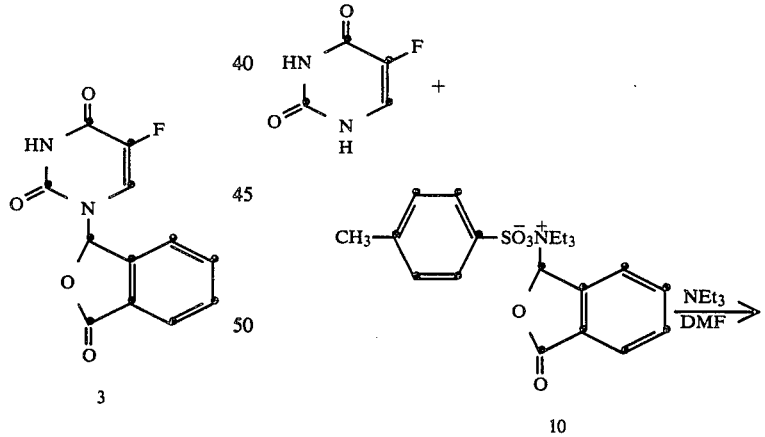

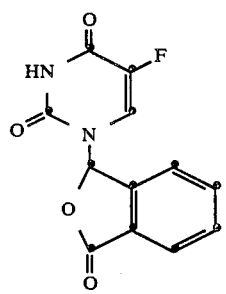

The compound 10 as crude product provided in the above step (1) and 0.774 g (5.95 mmol) of 5-FU are dissolved in 14 ml of anhydrous dimethylformamide to which is added 83 μl (0.60 mmol) of triethylamine is allowed to react at room temperature for 15 hours; the reaction mixture is poured into 140 ml of ice-water containing 3 ml of 2N hydrochloric acid and stirred for 30 minutes. The precipitating crystals are filtered to give 1.50 g of the titled compound 3 (Yield: 96%).

EXAMPLE 8

(1) Preparation of 4-ethyl-4-(3-oxo-1,3-dihydro-1-isobenzofuranyl)morpholinium bromide

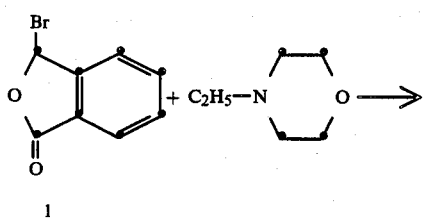

1

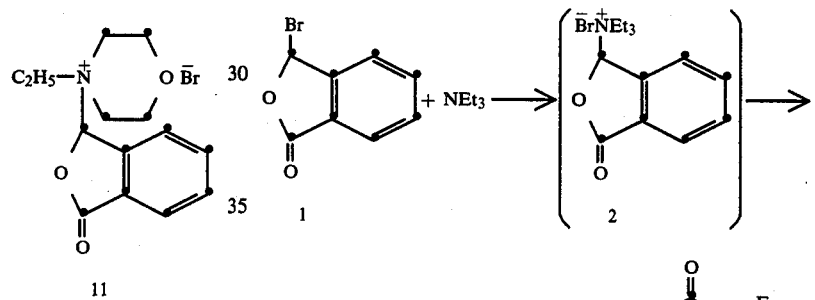

11

A solution of 2.13 g (10 mmol) of 3-bromo-1,3-dihydro-1-isobenzofuranone 1 and 1.27 ml (10 mmol) of N-ethylmorpholine in 21 ml of acetonitrile is allowed to react with stirring under reflux for 3 hours. The mixture is cooled and the precipitating crystals are filtered and washed with ether to give 2.36 g of the titled compound 11 (Yield: 72%).

m.p. 163°–168° C. (dec.).

NMR: δ d₆DMSO 1.21 (t, J=7 Hz, 3H), 3.5–4.2 (m, 10H), 7.30 (s, 1H), 7.83–8.30 (m, 4H).

(2) Preparation of 1-(3-oxo-1,3-dihydro-1-isobenzofuranyl)-5-fluorouracil

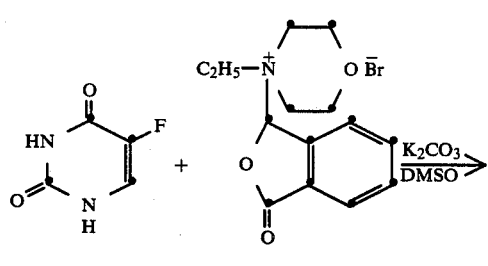

11

-continued

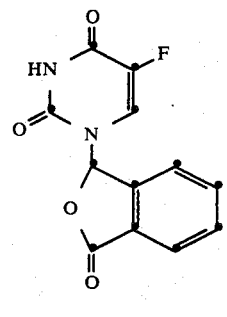

3

In the same manner as in Example 3-(2), a mixture of the compound 11 provided in the above step (1) and 5-FU in dimethylsulfoxide is allowed to react in the presence of 1 equimolar amount of anhydrous potassium carbonate at room temperature to give the titled compound 3 in good yield.

EXAMPLE 9

Preparation of 1-(3-oxo-1,3-dihydro-1-isobenzofuranyl)-5-fluorouracil

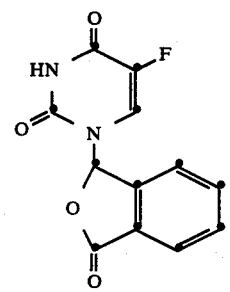

3

To a solution of 7.67 g (36 mmol) of 3-bromo-1,3-dihydro-1-isobenzofuranone 1 in 60 ml of dimethylformamide is added 5.01 ml (36 mmol) of triethylamine under ice-cooling and the mixture is allowed to react under ice-cooling for 1 hour and then at room temperature for 3 hours. The reaction mixture to which are added 3.90 g (30 mmol) of 5-FU and 1.25 ml (9 mmol) of triethylamine, is allowed to react with stirring at room temperature for 15 hours. The reaction mixture is poured into ice-water containing 10 ml of 2N hydrochloric acid and stirred for about 15 minutes, and the resulting crystals are collected by filtration, washed with water (50 ml×3), methanol (50 ml×1), and ether (50 ml×1), and dried to give 6.89 g of the titled compound 3 (Yield: 88%).

In the same manner as above, the reaction of the compound 2 with 5-FU is carried out in the presence of 1 mole equivalent (to 5-FU) of anhydrous potassium carbonate in place of triethylamine to give a favourable result.

EXAMPLE 10

Preparation of 1-(3-oxo-1,3-dihydro-1-isobenzofuranyl)-5-fluorouracil

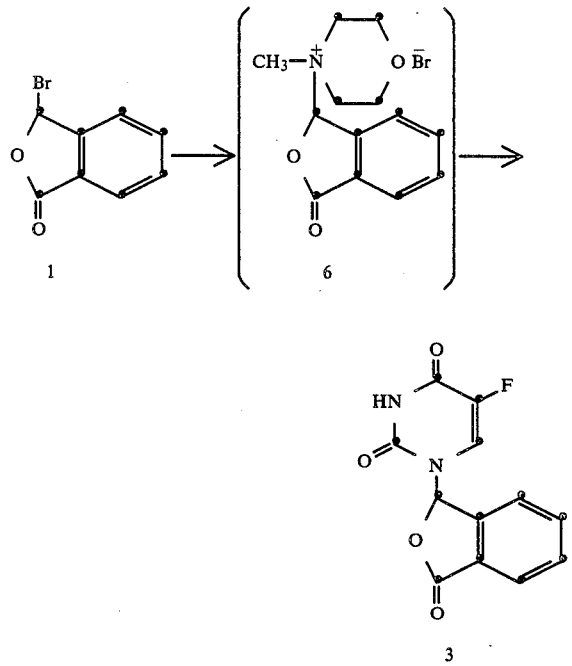

To a solution of 11.5 g (54 mmol) of 3-bromo-1,3-dihydro-1-isobenzofuranone 1 in 100 ml of dimethylformamide is added 5.94 ml (54 mmol) of N-methylmorpholine under ice-cooling and the mixture is allowed to react under ice-cooling for 15 minutes and then at room temperature for 2 hours with stirring, during which time the crystals of the product 4-methyl-4-(3-oxo-1,3-dihydro-1-isobenzofuranyl)morpholinium bromide is precipitated. This suspension is mixed with 5.85 g (45 mmol) of 5-FU and 6.22 g (45 mmol) of anhydrous potassium carbonate, and allowed to react with stirring well for 15 hours. The reaction mixture is poured into about 1 L of ice-water containing 45 ml of 2N hydrochloric acid and stirred for 15 minutes, and the precipitating crystals are collected by filtration, washed with water (50 ml×3), methanol (50 ml×1), and ether (50 ml×1), and dried to give 11.20 g of the titled compound 3 (Yield: 95%).

EXAMPLE 11

Preparation of 1-(3-oxo-1,3-dihydro-1-isobenzofuranyl)-5-fluorouracil

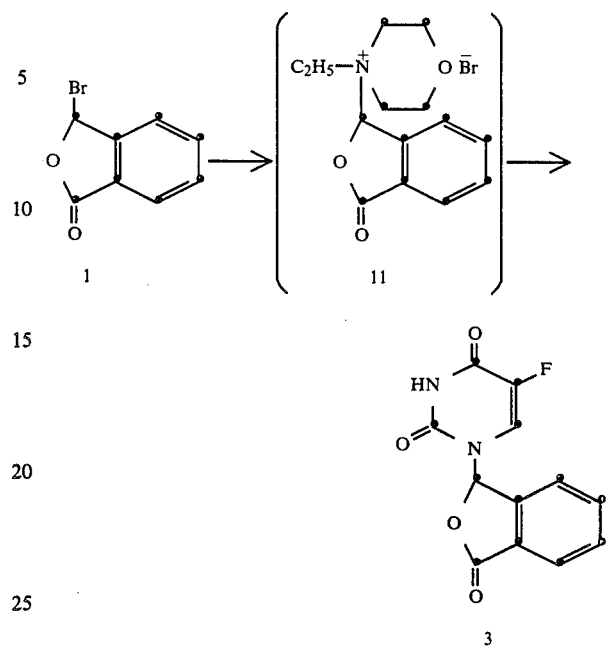

To a solution of 6.39 g (30 mmol) of 3-bromo-1,3-dihydro-1-isobenzofuranone 1 in 96 ml of dimethylformamide is added 3.82 ml (30 mmol) of N-ethylmorpholine, and the mixture is allowed to react with stirring for 3 hours. The reaction mixture to which are added 3.9 g (30 mmol) of 5-FU and 0.38 ml (3 mmol) of N-ethylmorpholine is allowed to react with stirring at room temperature for 40 hours. The reaction mixture is poured into 960 ml of ice-water containing 15 ml of 2N hydrochloric acid and stirred for about 15 minutes, and the precipitating crystals are collected by filtration, washed with water (50 ml×3), methanol (50 ml×1), and ether (50 ml×1), and dried to give 5.70 g of the titled compound 3 (Yield: 73%).

In the same manner as above, the reaction of the compound 11 with 5-FU is carried out in the presence of 1 mole equivalent (to 5-FU) of anhydrous potassium carbonate in place of N-ethylmorpholine to give a favourable result.

What we claim is:

1. A process for producing a 1-phthalidyl-5-fluorouracil of the formula

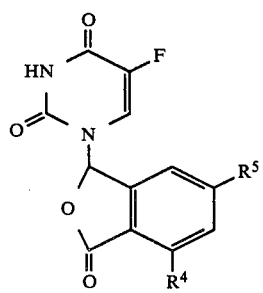

wherein $R^4$ and $R^5$ each represents hydrogen, trialkylsilyloxy, alkoxy, nitro, cyano, carboxy or alkoxycarbonyl which consists essentially of reacting a phthalidyl compound of the formula:

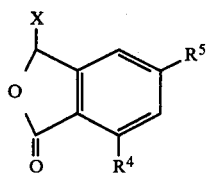

wherein
X represents halogen, trihalogenoacetyloxy, alkylsulfonyloxy or arylsulfonyloxy; and
R⁴ and R⁵ each has the same significance as defined above with a tertiary amine of the formula:

wherein
R¹, R² and R³ each represents alkyl, or R¹ represents alkyl, and R² and R³ taken together with the adjacent nitrogen atom form a saturated 5- or 6-membered ring which may contain an oxygen, or

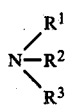

represents quinuclidine, to yield a phthalidylammonium compound of the formula

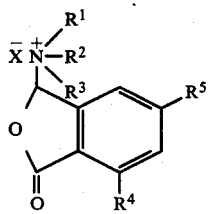

wherein
X, R¹, R², R³, R⁴ and R⁵ each has the same significance as defined above
and reacting the latter with 5-fluorouracil.

2. A process for producing a 1-phthalidyl-5-fluorouracil of the formula:

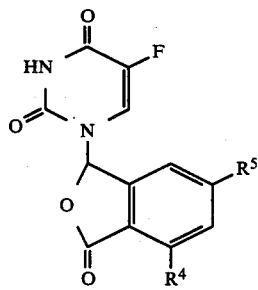

wherein
R⁴ and R⁵ each represents hydrogen, trialkylsilyloxy, alkoxy, nitro, cyano, carboxy, or alkoxycarbonyl, which consists essentially of reacting a phthalidylammonium compound of the formula:

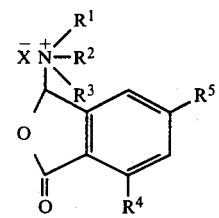

wherein
X represents halogen, trihalogenoacetyloxy, alkylsylfonyloxy or arylsulfonyloxy;
R¹, R² and R³ each represents alkyl, or R¹ represents alkyl, and R² and R³ taken together with the adjacent nitrogen atom form a saturated 5- or 6-membered ring which may contain an oxygen, or

represents quinuclidine; and
R⁴ and R⁵ each has the same significance as defined above with 5-fluorouracil.

3. A process claimed in claim 1, wherein the reaction of the phthalidyl compound with the tertiary amine is carried out in a solvent.

4. A process claimed in claim 3, wherein the tertiary amine is selected from the group consisting of triethylamine, N-methylmorpholine, and N-ethylmorpholine.

5. A process claimed in claim 3, wherein the solvent is selected from the group consisting of benzene, acetonitrile, tetrahydrofuran, dimethylformamide, and dimethylacetamide.

6. A process for producing a 1-phthalidyl-5-fluorouracil of the formula:

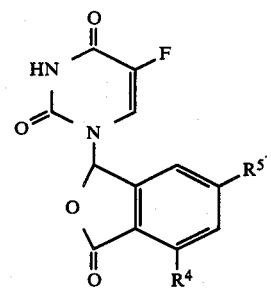

wherein
R⁴ and R⁵ each represents hydrogen, trialkylsilyloxy, alkoxy, nitro, cyano, carboxy, or alkoxycarbonyl which consists essentially of adding a tertiary amine of the formula:

wherein
R¹, R² and R³ each represents alkyl, or R¹ represents alkyl, and R² and R³ taken together with the adjacent nitrogen atom form a saturated 5- or 6-membered ring which may contain an oxygen, or

represents quinuclidine to a phthalidyl compound of the formula:

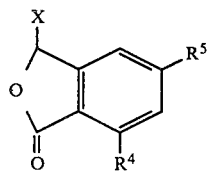

wherein
X represents halogen, trihalogenoacetyloxy, alkylsulfonyloxy or arylsulfonyloxy; and
$R^4$ and $R^5$ each has the same significance as defined above, and subsequently reacting the resultant product with 5-fluorouracil.

* * * * *